United States Patent
Lins et al.

(10) Patent No.: US 8,568,305 B2
(45) Date of Patent: Oct. 29, 2013

(54) MINIMALLY-INVASIVE PORTAL SYSTEM FOR PERFORMING LUMBAR DECOMPRESSION, INSTRUMENTED FUSION/STABILIZATION, AND THE LIKE

(75) Inventors: Robert E. Lins, Boca Raton, FL (US); Loren E. Lins, Boca Raton, FL (US); Harvey Simovitch, Boca Raton, FL (US)

(73) Assignee: US Spine, Inc., Salt Lake City, UT (US)

( * ) Notice: Subject to any disclaimer, the term of this patent is extended or adjusted under 35 U.S.C. 154(b) by 912 days.

(21) Appl. No.: 11/323,002

(22) Filed: Dec. 29, 2005

(65) Prior Publication Data
US 2006/0142642 A1 Jun. 29, 2006

Related U.S. Application Data

(60) Provisional application No. 60/639,936, filed on Dec. 29, 2004.

(51) Int. Cl.
*A61B 1/32* (2006.01)

(52) U.S. Cl.
USPC ............ 600/210; 600/201; 600/215; 600/233

(58) Field of Classification Search
USPC ......... 600/201, 204, 206, 208, 210, 213–216, 600/218, 219, 221, 225–227, 231, 233, 234
See application file for complete search history.

(56) References Cited

U.S. PATENT DOCUMENTS

| | | | | |
|---|---|---|---|---|
| 497,064 A * | 5/1893 | Van Meter | ..................... | 600/234 |
| 1,796,072 A * | 3/1931 | Baer | ............................ | 600/219 |
| 2,300,040 A * | 10/1942 | Betts | .............................. | 600/220 |
| 2,623,517 A * | 12/1952 | Barlow et al. | ................. | 600/233 |
| 3,070,088 A * | 12/1962 | Brahos | ........................... | 600/234 |
| 3,463,144 A * | 8/1969 | Hammond | .................... | 600/210 |
| 3,965,890 A * | 6/1976 | Gauthier | ....................... | 600/215 |
| 5,231,974 A * | 8/1993 | Giglio et al. | .................. | 600/206 |
| 5,520,610 A * | 5/1996 | Giglio et al. | .................. | 600/233 |
| 5,688,223 A * | 11/1997 | Rosendahl | .................... | 600/215 |
| 5,980,569 A * | 11/1999 | Scirica | ............................... | 606/1 |
| 6,102,853 A * | 8/2000 | Scirica et al. | ................. | 600/227 |
| 6,113,535 A * | 9/2000 | Fox et al. | ....................... | 600/228 |
| 6,206,826 B1 * | 3/2001 | Mathews et al. | .............. | 600/210 |
| 6,254,533 B1 * | 7/2001 | Fadem et al. | .................. | 600/208 |
| 2004/0176665 A1 * | 9/2004 | Branch et al. | ................. | 600/210 |
| 2004/0230100 A1 * | 11/2004 | Shluzas | ......................... | 600/208 |
| 2005/0159651 A1 * | 7/2005 | Raymond et al. | ............. | 600/213 |
| 2006/0135852 A1 * | 6/2006 | Koros et al. | .................... | 600/234 |
| 2006/0142642 A1 * | 6/2006 | Lins et al. | ...................... | 600/210 |

* cited by examiner

*Primary Examiner* — Kevin T Truong
*Assistant Examiner* — Christian Sevilla
(74) *Attorney, Agent, or Firm* — Phillps Ryther & Winchester; Matthew D. Thayne

(57) ABSTRACT

The present invention provides a minimally-invasive portal system for performing lumbar decompression, instrumented fusion/stabilization, and the like. The minimally-invasive portal system utilizes an access tube having an adjustable cross-sectional area and one or more retractor devices each having a first portion and a second portion aligned at a predetermined angle relative to the first portion, wherein the first portion of each of the one or more retractor devices is disposed substantially concentrically with the access tube, and wherein the second portion of each of the one or more retractor devices protrudes substantially beyond a bottom portion of the access tube. The minimally-invasive portal system also utilizes a plurality of adjustment mechanisms for selectively adjusting the cross-sectional area of the access tube and one or more retaining clips for securing the one or more retractor devices to the access tube in a fixed position.

9 Claims, 10 Drawing Sheets

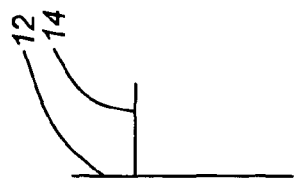
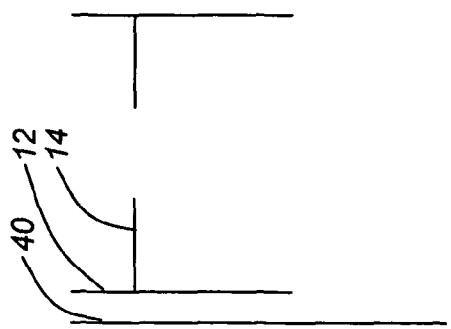
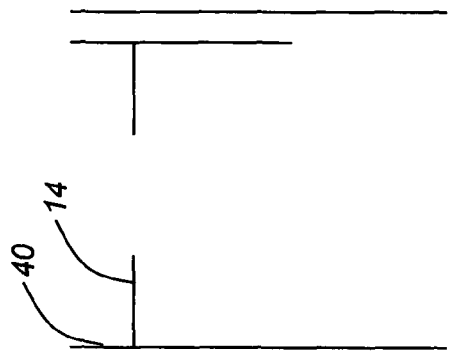
FIG. 2.

MINIMALLY-INVASIVE PORTAL SYSTEM FOR PERFORMING LUMBAR DECOMPRESSION, INSTRUMENTED FUSION/STABILIZATION, AND THE LIKE

CROSS-REFERENCE TO RELATED APPLICATION(S)

The present non-provisional patent application claims the benefit of priority of U.S. Provisional Patent Application No. 60/639,936, filed Dec. 29, 2004, and entitled "MINIMALLY-INVASIVE PORTAL SYSTEM FOR PERFORMING LUMBAR DECOMPRESSION, INSTRUMENTED FUSION/STABILIZATION, AND THE LIKE," which is incorporated in-full by reference herein.

FIELD OF THE INVENTION

The present invention relates generally to the medical and surgical fields. More specifically, the present invention relates to a minimally-invasive portal system for performing lumbar decompression, instrumented fusion/stabilization, and the like. Advantageously, the minimally-invasive portal system of the present invention provides enhanced access to and visualization of an area of interest within the body of a human patient, a veterinary patient, or the like, such that a surgical procedure may be performed, especially a surgical procedure involving the lumbar or cervical spine of the patient.

BACKGROUND OF THE INVENTION

Various portal systems exist in the prior art for providing access to and visualization of an area of interest within the body of a human patient, a veterinary patient, or the like, such that a surgical procedure may be performed, especially a surgical procedure involving the lumbar or cervical spine of the patient. However, none of these portal systems are capable of being inserted and/or adjusted such that they are sufficiently minimally invasive. Advantageously, minimally-invasive medical and surgical systems and procedures result in as little damage and trauma to adjacent anatomical structures as possible, thus minimizing discomfort and speeding recovery. For example, it is important in surgical procedures involving the lumbar or cervical spine of a patient to minimize damage and trauma to the skin, musculature, and ligaments adjacent to the spine. Of primary importance, however, is providing an adequate field of view.

Thus, what is needed is an improved minimally-invasive portal system that provides enhanced access to and visualization of an area of interest within the body of a human patient, a veterinary patient, or the like, such that a surgical procedure may be performed, especially a surgical procedure involving the lumbar or cervical spine of the patient. The minimally-invasive portal system should be relatively simple to insert, adjust, and remove, and should provide an adequate field of view.

BRIEF SUMMARY OF THE INVENTION

In various exemplary embodiments, the present invention provides a minimally-invasive portal system that provides enhanced access to and visualization of an area of interest within the body of a human patient, a veterinary patient, or the like, such that a surgical procedure may be performed, especially a surgical procedure involving the lumbar or cervical spine of the patient. Advantageously, the minimally-invasive portal system of the present invention is relatively simple to insert, adjust, and remove, and provides an adequate field of view.

In one exemplary embodiment of the present invention, a minimally-invasive portal system for performing a medical or surgical procedure includes an access tube having a selectively adjustable cross-sectional area; and one or more retractor devices each having a first portion and a second portion aligned at a predetermined angle relative to the first portion, wherein the first portion of each of the one or more retractor devices is disposed substantially concentrically with the access tube, and wherein the second portion of each of the one or more retractor devices protrudes substantially beyond a bottom portion of the access tube.

In another exemplary embodiment of the present invention, a minimally-invasive portal system for performing a medical or surgical procedure includes an access tube having a selectively adjustable cross-sectional area; a plurality of adjustment mechanisms coupled to the access tube for selectively adjusting the cross-sectional area of the access tube; and one or more retractor devices each having a first portion and a second portion aligned at a predetermined angle relative to the first portion, wherein the first portion of each of the one or more retractor devices is disposed substantially concentrically with the access tube, and wherein the second portion of each of the one or more retractor devices protrudes substantially beyond a bottom portion of the access tube.

In a further exemplary embodiment of the present invention, a minimally-invasive method for performing a medical or surgical procedure includes disposing an access tube having a selectively adjustable cross-sectional area at least partially with the body of a patient; and disposing one or more retractor devices each having a first portion and a second portion aligned at a predetermined angle relative to the first portion at least partially within an interior volume defined by the access tube, wherein the first portion of each of the one or more retractor devices is disposed substantially concentrically with the access tube, and wherein the second portion of each of the one or more retractor devices protrudes substantially beyond a bottom portion of the access tube.

BRIEF DESCRIPTION OF THE DRAWINGS

The present invention is illustrated and described herein with reference to the various drawings, in which like reference numbers denote like system components or method steps, and in which:

FIG. 2 is a series of cross-sectional side views illustrating several exemplary steps in the insertion of the minimally-invasive portal system of FIG. 1;

DETAILED DESCRIPTION OF THE INVENTION

In various exemplary embodiments, the present invention provides a minimally-invasive portal system that provides enhanced access to and visualization of an area of interest within the body of a human patient, a veterinary patient, or the like, such that a surgical procedure may be performed, especially a surgical procedure involving the lumbar or cervical spine of the patient. Advantageously, the minimally-invasive portal system of the present invention is relatively simple to insert, adjust, and remove, and provides an adequate field of view.

Figure 1:
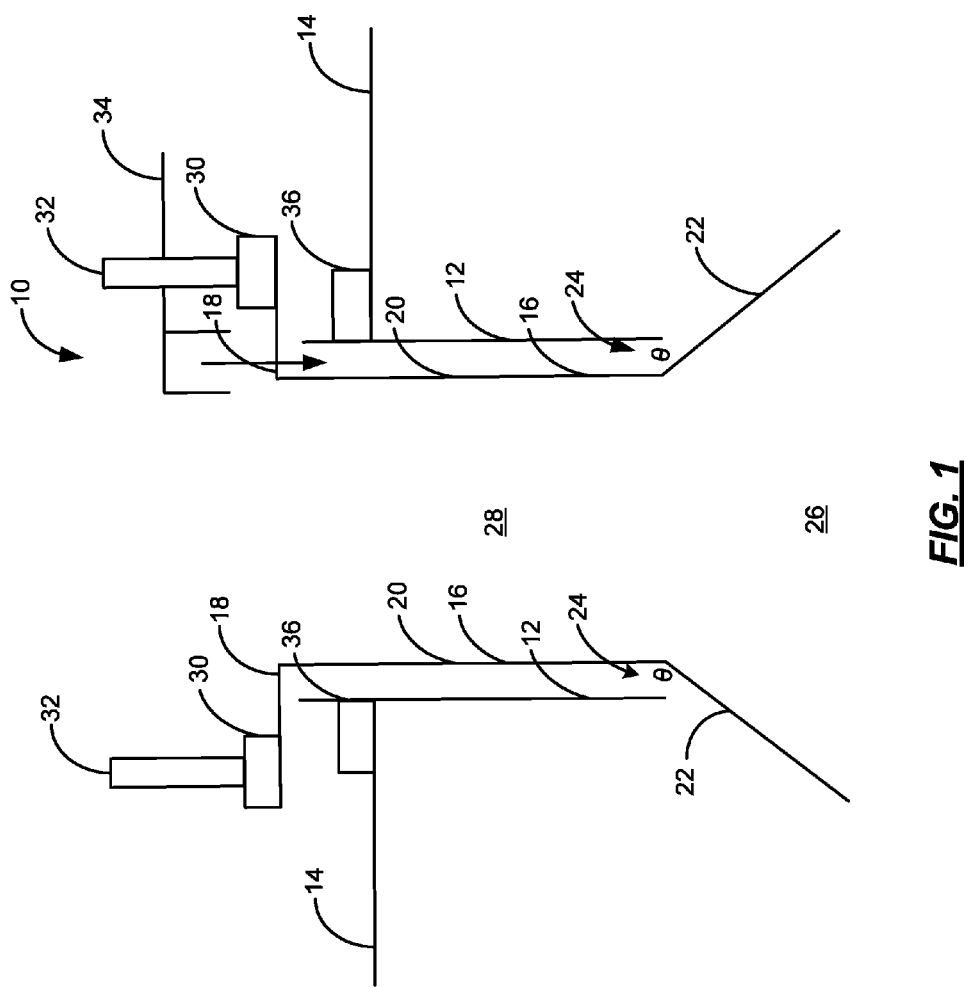
FIG. 1 is a cross-sectional side view illustrating one exemplary embodiment of the minimally-invasive portal system of the present invention, the minimally-invasive portal system including an access tube, one or more retractor devices, one or more retaining clips, and a plurality of adjustment mechanisms that assist a user (doctor/surgeon) in visualizing and gaining access to an area within the body of a patient.

Referring to FIG. 1, in one exemplary embodiment of the present invention, the minimally-invasive portal system 10 includes an access tube 12 that is selectively positioned through the skin 14 of a patient adjacent to an area of interest (i.e. an area to be operated on or otherwise visualized). Optionally, the access tube 12 may be positioned using one or more conventional dilation tubes, well known to those of ordinary skill in the art, for successively dilating the skin 14 and musculature of the patient to greater diameters or dimensions. Preferably, the access tube 12 has a substantially circular, oval-shaped, square-shaped, or rectangular cross-sectional shape, although other suitable cross-sectional shapes may be utilized. Likewise, the access tube 12 may have any suitable diameter, dimension, and/or depth suitable for the procedure to be performed.

One or more retractor devices 16 are selectively disposed concentrically within/through the access tube 12. Each of the one or more retractor devices 16 includes a top portion 18 which remains external to the body of the patient, a central portion 20 which is disposed concentrically within the access tube 12, and a bottom portion 22 which is disposed through and protrudes beneath the access tube 12 into the body of the patient. The bottom portion 22 of each of the one or more retractor devices 16 is disposed at a predetermined angle (θ) 24 relative to the central portion 20 of each of the one or more retractor devices 16, the predetermined angle (θ) 24 varying from about 0 degrees to about 45 degrees, in an exemplary embodiment of the present invention. Optionally, the predetermined angle (θ) 24 is adjustable during the procedure to be performed. It should be noted that the central portion 20 and the bottom portion 22 of each of the one or more retractor devices 16 may be sized and/or shaped such that they fit comfortably within/through the access tube 12 and provide visualization of/access to an exposed area 26 via a portal 28. Preferably, the top portion 18 of each of the one or more retractor devices 16 includes a post 30 and handle 32, which may be selectively removable.

In use, one or more retaining clips 34 (described in greater detail herein below) may be used to selectively couple the one or more retractor devices 16 to the access tube 12. Preferably, the access tube 12 incorporates one or more adjustment mechanisms 36 (also described in greater detail herein below). The one or more adjustment mechanisms 36 are each operable for selectively adjusting the diameter or dimensions of the access tube 12, and, correspondingly, the separation of the one or more retractor devices 16, the diameter or dimensions of the portal 28, and the diameter or dimensions of the exposed area 26, providing visualization and/or access flexibility.

Referring to FIG. 2, as described above, the access tube 12 may be positioned using one or more conventional dilation tubes 40, well known to those of ordinary skill in the art, for successively dilating the skin 14 and musculature of the patient to greater diameters or dimensions. The dilation tube(s) 40 is/are first inserted through the skin 14 and musculature of the patient, either singly or successively. The access tube 12 is then disposed concentrically about the dilation tube(s) 40. Finally, the dilation tube(s) 40 is/are removed, leaving the access tube 12 in place. The one or more retractor devices 16 (FIG. 1) are then inserted (not shown in FIG. 2) and the appropriate adjustments are made using the one or more adjustment mechanisms 36 (FIG. 1).

Figure 3:
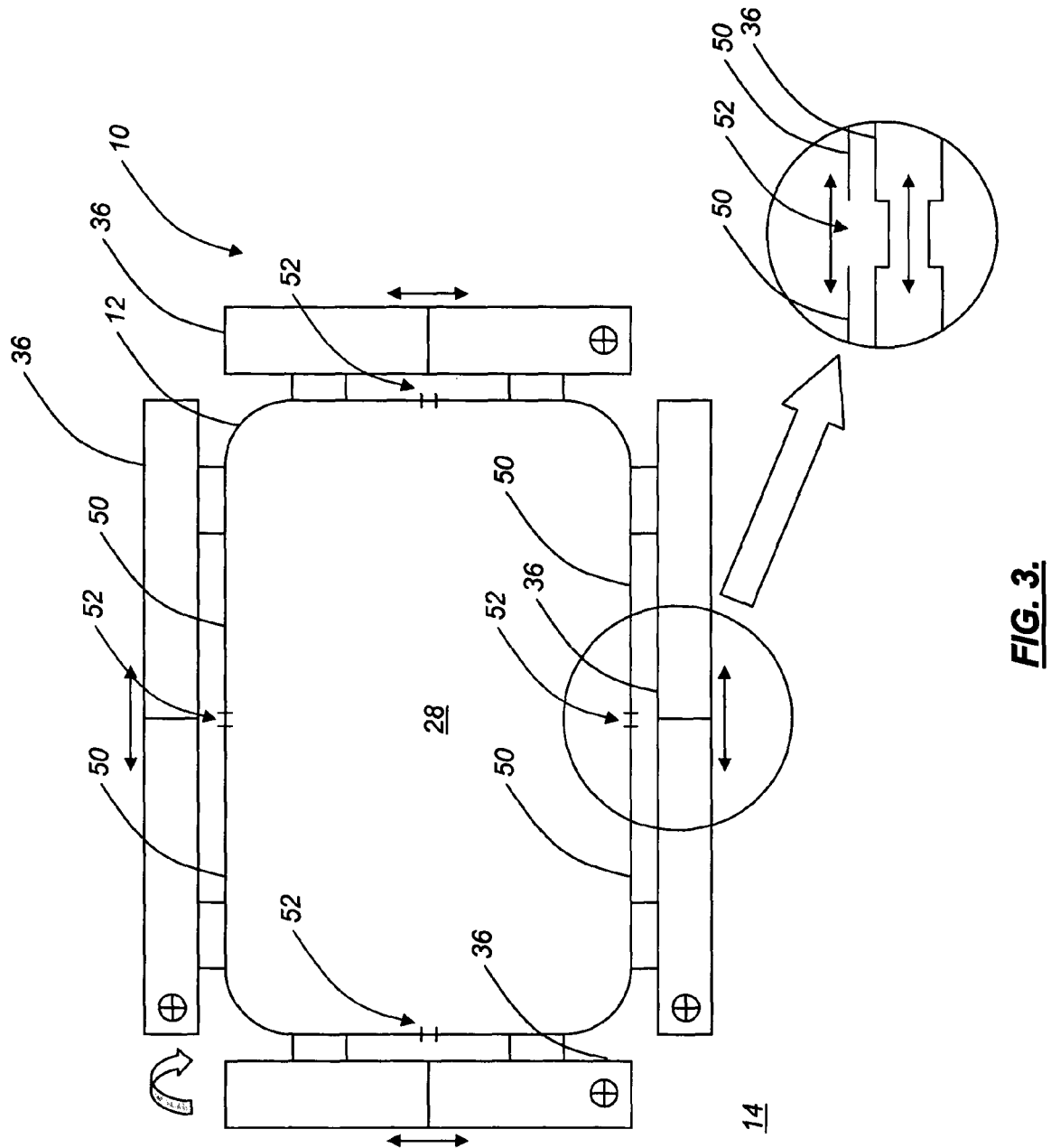
FIG. 3 is a planar top view illustrating the minimally-invasive portal system of FIG. 1, specifically a single-level configuration of the minimally-invasive portal system.

Referring to FIG. 3, in another exemplary embodiment of the present invention, the access tube 12 consists of a plurality of segments 50 which are selectively adjustable relative to one another via a plurality of adjustment areas 52. When adjusted, the plurality of segments 50 of the access tube 12 may separate from one another (as shown in FIG. 3), or they may overlap in the plurality of adjustment areas 52 (not shown in FIG. 3). Alternatively, a portion of one of the plurality of segments 50 may be substantially disposed within and move relative to another one of the plurality of segments 50. The plurality of segments 50 of the access tube 12 are selectively adjustable relative to one another using the one or more adjustment mechanisms 36 (described in greater detail herein below). Again, the one or more adjustment mechanisms 36 are each operable for selectively adjusting the diameter or dimensions of the access tube 12, and, correspondingly, the separation of the one or more retractor devices 16 (FIG. 1), the diameter or dimensions of the portal 28, and the diameter or dimensions of the exposed area 26 (FIG. 1), providing visualization and/or access flexibility. It should be noted that a single-level configuration of the minimally-invasive portal system 10 of the present invention is shown in FIG. 3, meaning that there is one adjustment area 52 for any given portion or "side" of the access tube 12.

Figure 4:
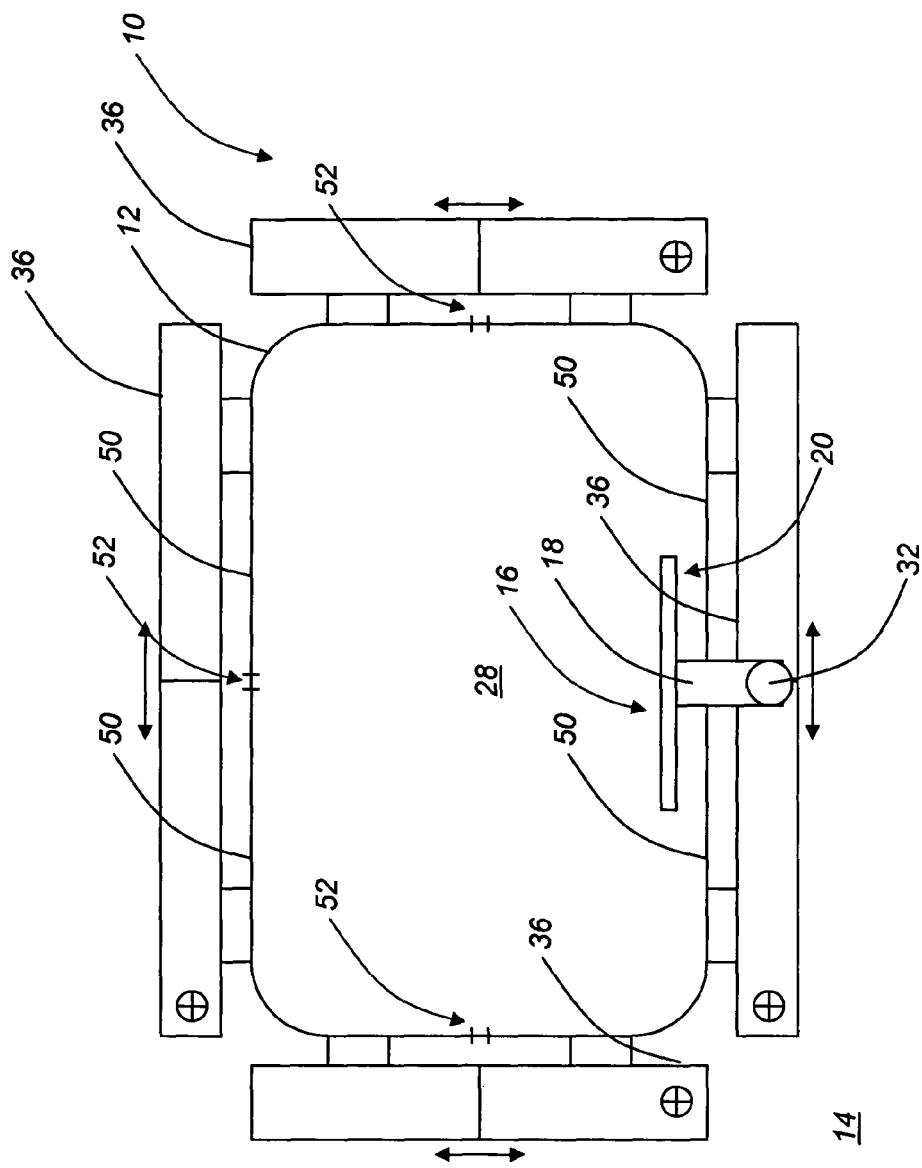
FIG. 4 is another planar top view illustrating the minimally-invasive portal system of FIGS. 1 and 3, the figure including the placement of a retractor device.

Referring to FIG. 4, the single-level configuration of the minimally-invasive portal system 10 of the present invention is shown with one retractor device 16 in place. Again, each of the one or more retractor devices 16 includes a top portion 18 which remains external to the body of the patient and a central portion 20 which is disposed concentrically within the access tube 12. Preferably, the top portion 18 of each of the one or more retractor devices 16 includes a handle 32, which may be selectively removable. The handle 32 allows a user to effectively grasp and manipulate the retractor device 16. It should be noted that, although one retractor device 16 is shown in FIG. 4, more than one retractor device 16 may be used. It should also be noted that the one or more retaining clips 34 (FIG. 1) (described in greater detail herein below) that are used to selectively couple the one or more retractor devices 16 to the access tube 12 are not shown in FIG. 4.

Figure 5:
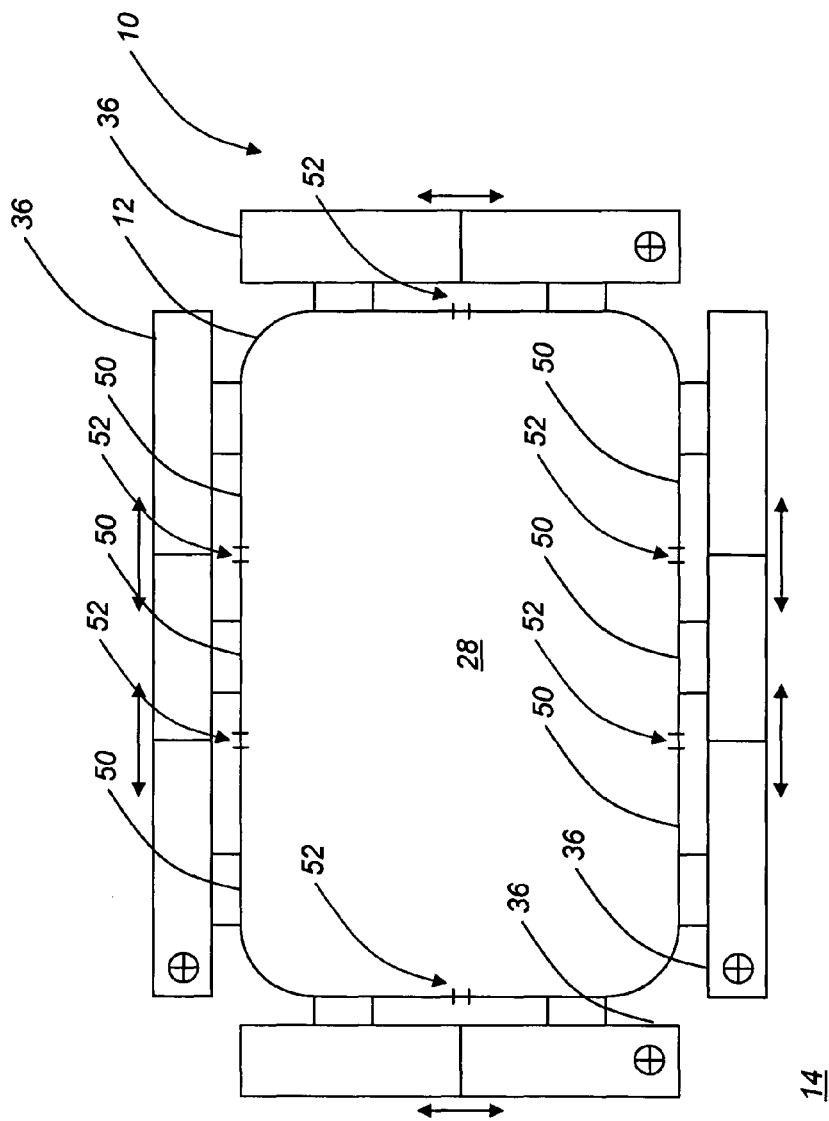
FIG. 5 is a further planar top view illustrating the minimally-invasive portal system of FIG. 1, specifically a multi-level configuration of the minimally-invasive portal system.

Referring to FIG. 5, in a further exemplary embodiment of the present invention, a multi-level configuration of the minimally-invasive portal system 10 includes a plurality of adjustment areas 52 for one or more portions or "sides" of the access tube 12, providing enhanced adjustment flexibility.

Figure 6:
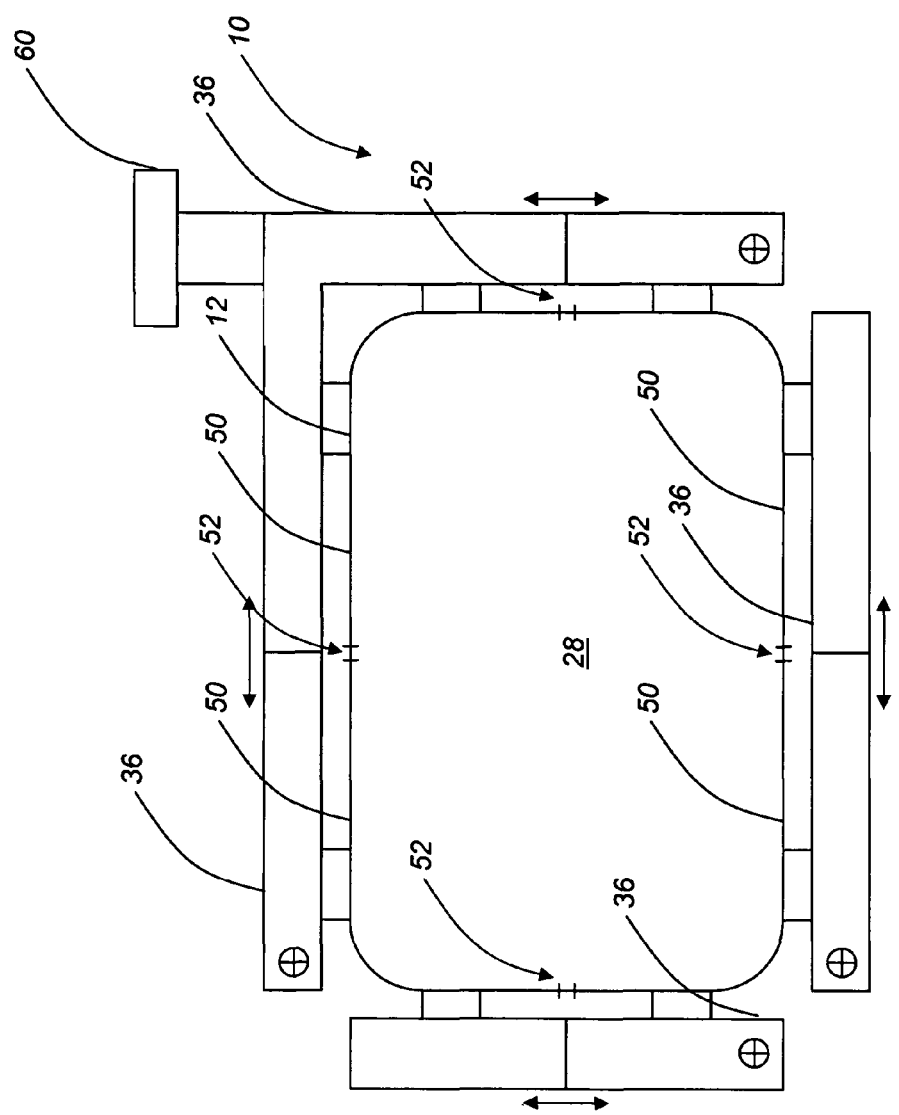
FIG. 6 is a still further planar top view illustrating the minimally-invasive portal system of FIGS. 1, 3, and 4, the minimally-invasive portal system incorporating an optional handle attachment.
Figure 7:
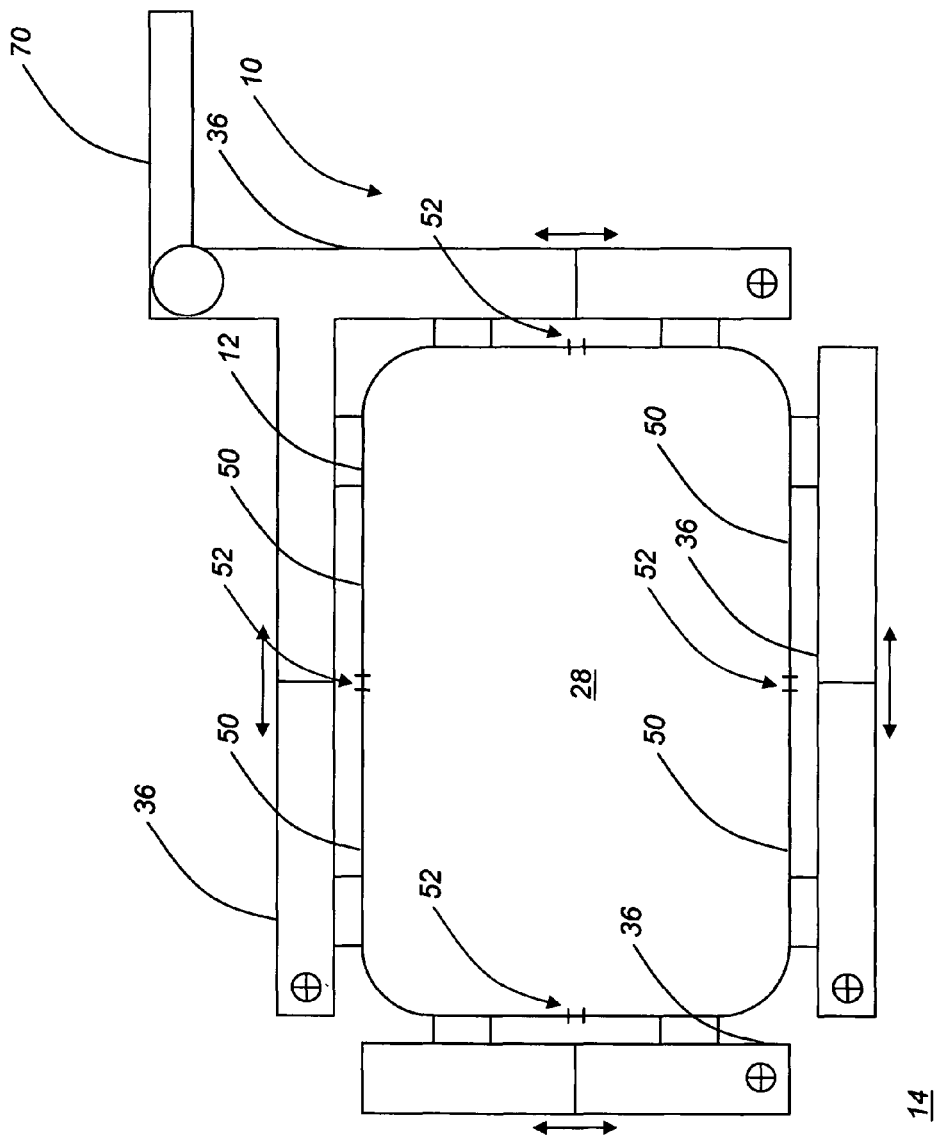
FIG. 7 is a still further planar top view illustrating the minimally-invasive portal system of FIGS. 1, 3, and 4, the minimally-invasive portal system incorporating an optional adjustable table attachment.

Referring to FIGS. 6 and 7, in two still further exemplary embodiments of the present invention, the minimally-invasive portal system 10 includes either a handle attachment 60 (FIG. 6) or a table attachment 70 (FIG. 7) attached to the one or more adjustment mechanisms 36 and/or the access tube 12. Both the handle attachment 60 and the table attachment 70 protrude substantially upwardly and outwardly from the one or more attachment mechanisms 36 and/or the access tube 12. The handle attachment 60 allows a user to effectively grasp and manipulate the one or more attachment mechanisms 36 and/or the access tube 12. Likewise, the table attachment 70 allows the one or more attachment mechanisms 36 and/or the access tube 12 to be securely fastened to an operating table or the like, thereby effectively stabilizing the minimally-invasive portal system 10 of the present invention.

Figure 8:
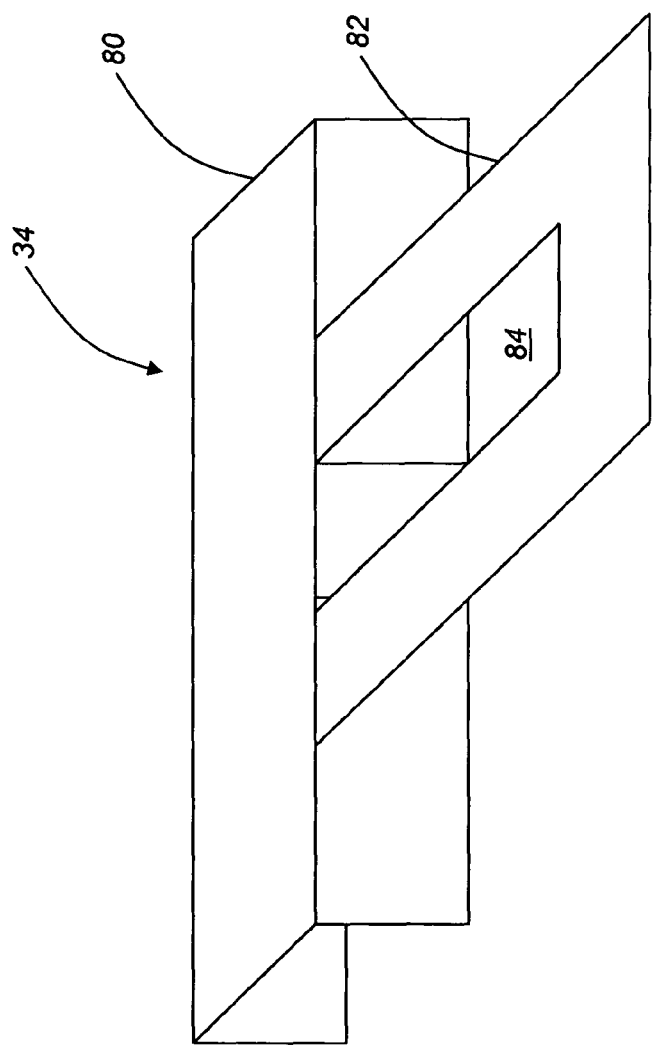
FIG. 8 is a perspective view illustrating one exemplary embodiment of the one or more retaining clips of FIG. 1.

Referring to FIG. 8, each of the one or more retaining clips 34 includes a body portion 80 and a tongue portion 82. The body portion 80 of each of the one or more retaining clips 34 is substantially U-shaped, or has another suitable shape for selectively coupling the one or more retractor devices 16 (FIGS. 1 and 4) to the access tube 12 (FIGS. 1-7). The tongue portion 82 of each of the one or more retaining clips 34 defines an opening 84 through which the post 30 (FIGS. 1 and 4) and handle 32 (FIGS. 1 and 4) of each of the one or more retractor devices 16 may pass. In use, the tongue portion 82 of the retaining clip 34 is grasped with the thumb and index finger of the user, advanced downward over the post 30 and handle 32 of the retractor device 16, and engages/retains the retractor device 16.

Figure 9:
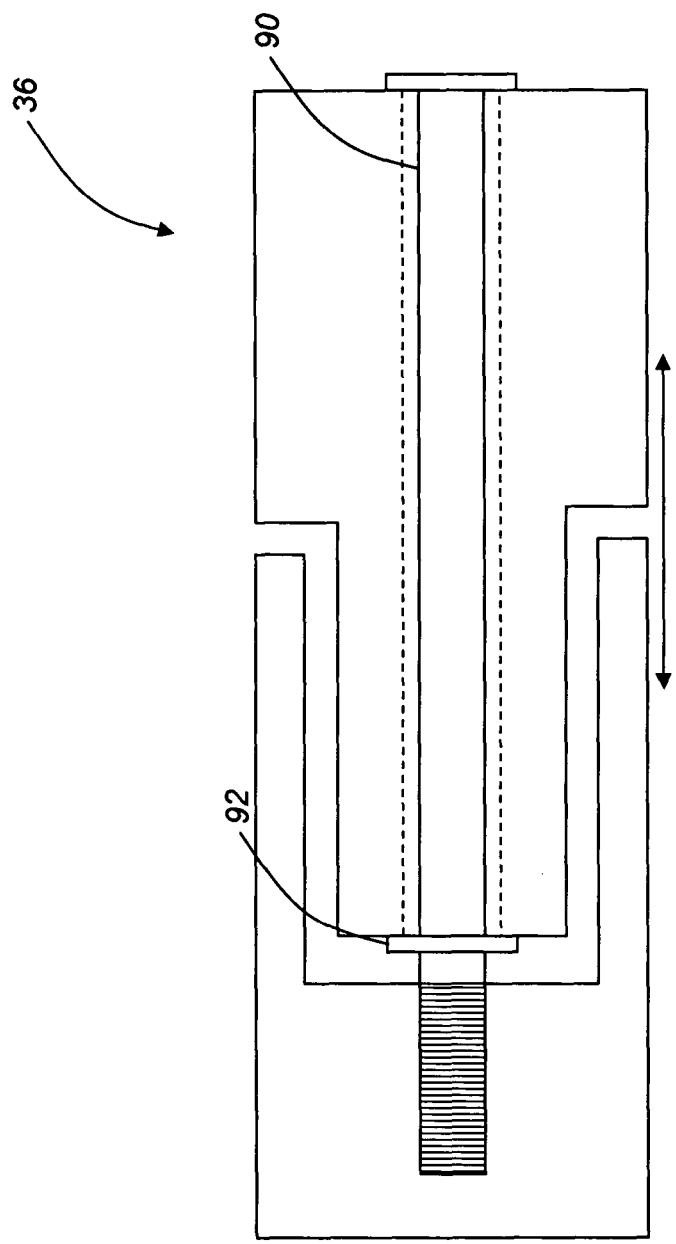
FIG. 9 is a cross-sectional side view illustrating one exemplary embodiment of the plurality of adjustment mechanisms of FIGS. 1 and 3-7.
Figure 10:
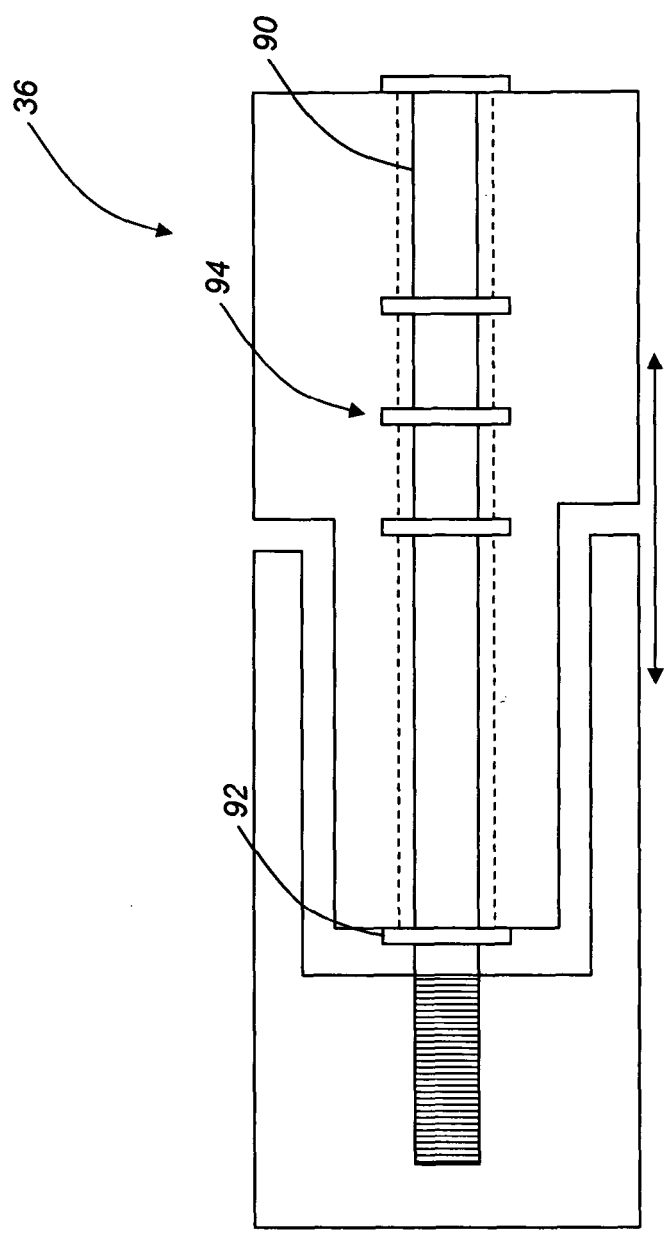
FIG. 10 is another cross-sectional side view illustrating another exemplary embodiment of the plurality of adjustment mechanisms of FIGS. 1 and 3-7.

FIGS. 9 and 10 show two exemplary embodiments of the adjustment mechanism 36 of the present invention. In general, the adjustment mechanism 36 may consist of an extendable/retractable device that is suitable for selectively adjusting the diameter/dimensions of the access tube 12 (FIGS. 1-8). For example, FIG. 9 shows an adjustment mechanism 36 that incorporates a screw 90 and a retaining band 92. FIG. 10 shows an adjustment mechanism 36 that incorporates a screw 90, a retaining band 92, and one or more stabilizing bands 94.

It should be noted that any medically/surgically suitable materials may be used to manufacture the components of the minimally-invasive portal system of the present invention. Such materials are well known to those of ordinary skill in the art and may include, but are not limited to, suitable metals, plastics, and composite materials.

Although the present invention has been illustrated and described with reference to preferred embodiments and examples thereof, it will be readily apparent to those of ordinary skill in the art that other embodiments and/or examples may perform similar functions and/or achieve similar results. All such equivalent embodiments and examples are within the spirit and scope of the present invention and are intended to be covered by the following claims.

What is claimed is:

1. A minimally-invasive portal system for performing a medical or surgical procedure, comprising:
an access tube comprising a selectively adjustable cross-sectional area, wherein the cross-sectional area is adjustable in a first direction via at least one first adjustment mechanism and in a second direction substantially perpendicular to the first direction via at least one second adjustment mechanism, and wherein the access tube defines a depth;
a retractor device comprising a first portion and a second portion aligned at a predetermined angle relative to the first portion, wherein the first portion of the retractor device is configured to be disposed substantially concentrically within the access tube such that the access tube depth extends along substantially the entire length of the first portion of the retractor device, and wherein the second portion of the retractor device protrudes substantially beyond a bottom edge of the access tube, wherein the retractor device further comprises a third portion fixedly attached to a top region of the first portion, the third portion protruding outward beyond a top edge of the access tube, wherein the retractor device further comprises a handle portion attached to the third portion; and
one or more retaining clips configured to secure the retractor device to the access tube in a fixed position relative to one another, wherein each of the one or more retaining clips comprises a body portion and a tongue portion, wherein the body portion is substantially U-shaped and configured to simultaneously engage, within a region defined by the U-shaped body portion and in direct physical contact, the top edge of the access tube and the top region of the first portion of the retractor device during securement of the retractor device and the access tube, wherein the tongue portion at least partially defines an opening through which the handle portion of the retractor device protrudes during securement of the retractor device and the access tube by the U-shaped body portion of the clip.

2. The minimally-invasive portal system of claim 1, wherein the access tube comprises a plurality of segments, wherein the relative position of each of the plurality of segments is selectively adjustable relative to the remainder of the plurality of segments.

3. The minimally-invasive portal system of claim 1, wherein the predetermined angle is between about 0 degrees and about 45 degrees.

4. A minimally-invasive portal system for performing a medical or surgical procedure, comprising:
an access tube comprising a selectively adjustable cross-sectional area, wherein the cross-sectional area is adjustable in a first direction via a pair of first adjustment mechanisms and in a second direction substantially perpendicular to the first direction via a pair of second adjustment mechanisms;
a retractor device comprising a first portion and a second portion aligned at a predetermined angle relative to the first portion, wherein the first portion of the retractor device is configured to be disposed substantially concentrically within the access tube, and wherein the second portion of the retractor device protrudes substantially beyond a bottom edge of the access tube, wherein the retractor device further comprises a third portion fixedly attached to a top region of the first portion, the third portion protruding substantially beyond a top edge of the access tube, wherein the retractor device further comprises a handle portion attached to the third portion; and
one or more retaining clips configured to simultaneously engage the retractor device and the access tube to secure the retractor device and the access tube in a fixed position relative to one another, wherein each of the one or more retaining clips comprises a body portion and a tongue portion, wherein the body portion is substantially U-shaped and defines a channel configured to receive therein and simultaneously engage the top edge of the access tube and the top region of the first portion of the retractor device during securement of the retractor device and the access tube, wherein the tongue portion at least partially defines an opening through which the handle portion of the retractor device protrudes during securement of the retractor device and the access tube by the U-shaped body portion of the clip.

5. The minimally-invasive portal system of claim 4, wherein the access tube comprises a plurality of segments, wherein the relative position of each of the plurality of segments is selectively adjustable relative to the remainder of the plurality of segments.

6. The minimally-invasive portal system of claim 4, wherein the predetermined angle is between about 0 degrees and about 45 degrees.

7. A minimally-invasive method for performing a medical or surgical procedure, comprising:
   disposing an access tube at least partially within the body of a patient, wherein the access tube comprises a selectively adjustable cross-sectional area that is adjustable in a first direction via at least one first adjustment mechanism and in a second direction substantially perpendicular to the first direction via at least one second adjustment mechanism, and wherein the access tube defines a depth;
   disposing a retractor device at least partially within an interior volume defined by the access tube, the retractor device comprising a first portion, a second portion, and a third portion, wherein the first portion of the retractor device is disposed substantially concentrically within the access tube such that the access tube depth extends along substantially the entire length of the first portion of the retractor device, and wherein the second portion of each of the one or more retractor devices is aligned at a predetermined angle relative to the first portion and protrudes substantially beyond a bottom edge of the access tube, wherein the third portion is fixedly attached to a top region of the first portion, the third portion protruding substantially beyond a top edge of the access tube, wherein the retractor device further comprises a handle portion attached to the third portion; and
   securing the retractor device to the access tube in a fixed position using one or more retaining clips by positioning a body portion of the one or more retaining clips to simultaneously engage the top edge of the access tube and the top region of the first portion of the retractor device during securement of the retractor device and the access tube, wherein the retaining clip comprises a tongue portion that at least partially defines an opening through which the handle portion of the retractor device protrudes as the body portion simultaneously engages the top edge of the access tube and the top region of the first portion of the retractor device in direct physical contact.

8. The minimally-invasive method of claim 7, wherein the access tube comprises a plurality of segments, wherein the relative position of each of the plurality of segments is selectively adjustable relative to the remainder of the plurality of segments.

9. The minimally-invasive method of claim 7, wherein the predetermined angle is between about 0 degrees and about 45 degrees.

* * * * *